United States Patent [19]

Henkelmann et al.

[11] Patent Number: 5,252,755
[45] Date of Patent: Oct. 12, 1993

[54] PREPARATION OF 4-HYDROXYMETHYLTETRAHYDROPYRANS

[75] Inventors: Jochem Henkelmann; Thomas Ruehl, both of Ludwigshafen; Horst Zimmermann, Mannheim; Norbert Goetz; Wolfgang Spiegler, both of Worms; Thomas Kuekenhoehner, Boehl-Iggelheim, all of Fed. Rep. of Germany

[73] Assignee: BASF Aktiengesellschaft, Ludwigshafen, Fed. Rep. of Germany

[21] Appl. No.: 990,268

[22] Filed: Dec. 14, 1992

[30] Foreign Application Priority Data

Dec. 13, 1991 [DE] Fed. Rep. of Germany ....... 4141222

[51] Int. Cl.$^5$ .............................................. C07D 309/06
[52] U.S. Cl. ...................................................... 549/427
[58] Field of Search .................................. 549/427, 425

[56] References Cited

U.S. PATENT DOCUMENTS

| | | | |
|---|---|---|---|
| 2,479,283 | 8/1949 | Whetstone | 549/425 |
| 3,124,599 | 3/1964 | Guest et al. | 549/427 |
| 3,187,012 | 6/1965 | Dunlop et al. | 549/427 |

OTHER PUBLICATIONS

Chem. Abst., vol. 105, No. 17, Oct. 27, 1986, Abst. No. 152925e.

Rastether, JACS, 98, 6350–53 (1976).

*Primary Examiner*—Nicky Chan
*Attorney, Agent, or Firm*—Keil & Weinkauf

[57] ABSTRACT

A process for the preparation of 4-hydroxymethyltetrahydropyrans of the formula I

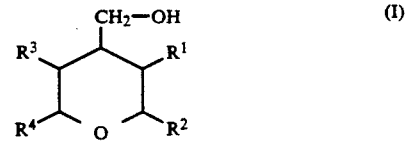

where $R^1$, $R^2$, $R^3$ and $R^4$ are hydrogen, $C_1$- to $C_{12}$-alkyl, $C_3$- to $C_8$-cycloalkyl, aryl or $C_7$- to $C_{20}$-aralkyl, comprises reacting a tetrahydropyrancarboxylic ester of the formula II

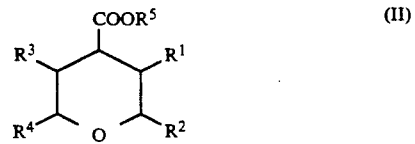

where $R^1$, $R^2$, $R^3$ and $R^4$ are as defined above, and $R^5$ is hydrogen or $C_1$- to $C_{12}$-alkyl, at from 50° to 400° C. and at from 1 to 400 bar in the presence of hydrogen and a hydrogenation catalyst.

3 Claims, No Drawings

PREPARATION OF 4-HYDROXYMETHYLTETRAHYDROPYRANS

The present invention relates to a process for the preparation of 4-hydroxymethyltetrahydropyrans by catalytic hydrogenation of tetrahydropyran-4-carboxylic esters.

The synthesis of 4-hydroxymethyltetrahydropyran from 4-methylenetetrahydropyran by epoxidation using hydrogen peroxide and reduction of the epoxide is disclosed in SU-A-84-3722686. In this process, the preparation of the starting compound causes problems due to double-bond isomerization.

4-Hydroxymethyltetrahydropyran can also be prepared by reduction of the corresponding aldehyde (J. Am. Chem. Soc., 98 (1976) 6350 to 6353). Here too, the preparation of the aldehyde is a multi-step synthesis.

It is an object of the present invention to overcome the abovementioned disadvantages and to develop a process which leads directly from tetrahydropyran-4-carboxylic esters to 4-hydroxymethyltetrahydropyrans.

We have found that this object is achieved by a novel and improved process for the preparation of 4-hydroxymethyltetrahydropyrans of the formula I

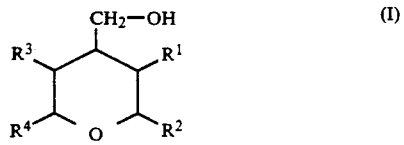

where $R^1$, $R^2$, $R^3$ and $R^4$ are hydrogen, $C_1$- to $C_{12}$-alkyl, $C_3$- to $C_8$-cycloalkyl, aryl or $C_7$- to $C_{20}$-aralkyl, which comprises reacting a tetrahydropyrancarboxylic ester of the formula II

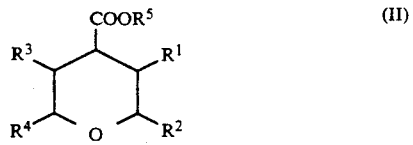

where $R^1$, $R^2$, $R^3$ and $R^4$ are as defined above, and $R^5$ is hydrogen or $C_1$- to $C_{12}$-alkyl, at from 50° to 400° C. and at from 1 to 400 bar in the presence of hydrogen and a hydrogenation catalyst.

The novel process can be carried out as follows:

The tetrahydropyran-4-carboxylic ester of the formula II can be converted into a hydroxymethyl compound of the formula I at elevated temperature using hydrogen in the presence of a hydrogenating catalyst.

The reaction can be carried out batchwise or continuously at from 50° to 400° C., preferably at from 150° to 350° C., in particular at from 180° to 260° C. The pressure during the reaction is from 1 to 400 bar, in particular from 50 to 300 bar.

The conversion of the tetrahydropyran-4-carboxylic ester II into the hydroxymethyl compound I can be carried out in the gas phase at from 50° to 400° C. and at from 1 to 400 bar or preferably in the liquid phase at from 50° to 400° C. and at from 1 to 400 bar. The weight hourly space velocity used is advantageously from 0.01 to 5 g, preferably from 0.2 to 1 g, particularly preferably from 0.05 to 0.5 g, of tetrahydropyran-4-carboxylic ester II per g of catalyst and per hour.

All the starting materials can be employed in the process according to the invention in solid, liquid or gaseous form.

The reaction can be carried out with upward or downward flow of the starting materials through the catalyst bed, which is generally fixed. It is also possible to employ a suspended catalyst. Examples of reactors which can be used are tubular reactors and tubebundle reactors.

The novel reaction can be carried out in the absence of solvents, but it may be advantageous to use solvents. Examples of solvents which can be used are water, ethers, such as diethyl ether, tetrahydrofuran and dioxane, aromatic compounds, such as benzene, toluene and the xylenes, chlorinated hydrocarbons, such as chloroform and methylene chloride, alcohols, for example $C_1$- to $C_8$-alkanols, preferably $C_1$- to $C_5$-alkanols, such as methanol, ethanol, n-propanol, isopropanol, the butanols and the pentanols, or mixtures of these. Particularly advantageous solvents are alcohols. The amount of solvent can be varied within broad limits and is preferably from 5 to 90% by weight, based on the tetrahydropyran-4-carboxylic ester II employed; the hydrogenation is particularly preferably carried out without a solvent.

The hydrogenation catalyst may be a conventional catalyst, as described, for example, in H. Kropf, Methoden der organischen Chemie (Houben-Weyl), Volume IV/1c, Georg Thieme Verlag, Stuttgart, 1980.

Preferred hydrogenation catalysts are those which contain copper and/or one or more metals from subgroup VII and/or VIII of the Periodic Table of the Elements, in particular nickel, cobalt, palladium, rhodium, platinum, ruthenium or rhenium. They can be employed either as supported catalyst or in compact form, i.e. without a support. Support materials which can be used are silicone dioxide, aluminum oxides, titanium oxides, activated charcoal, silicates and zeolites.

The conversion of the tetrahydropyran-4-carboxylic ester II in the liquid phase is carried out, for example, by heating a mixture of II and, if desired, a solvent to the desired reaction temperature under pressure in the presence of suspended hydrogenation catalyst and hydrogen. When the reaction is complete, the reaction mixture is cooled and decompressed, and the catalyst is removed, for example by filtration. The reaction mixture can subsequently be subjected, for example, to fractional distillation in order to isolate the desired hydroxymethyl compound I.

If, as is preferred, the reaction is carried out in the liquid phase in the presence of a hydrogenation catalyst in the form of a fixed bed, the tetrahydropyran-4-carboxylic ester II, if desired together with a solvent, is passed upward or downward through the hydrogenation catalyst under pressure in the presence of hydrogen. The hydrogenation product is cooled and decompressed and subsequently subjected, for example, to fractional distillation in order to isolate the hydroxymethyl compound II.

The substituents $R^1$, $R^2$, $R^3$, $R^4$ and $R^5$ in the compounds I and II are defined as follows:

$R^1$, $R^2$, $R^3$ and $R^4$
  independently of one another
  hydrogen,
  $C_1$- to $C_{12}$- alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyll n-hexyl, isohexyl, sec-hexyl, n-heptyl, isoheptyl, n-octyl, isooctyl, n-nonyl, isoundecyl, n-dodecyl or isodecyl, preferably $C_1$- to $C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl or isooctyl, particularly preferably $C_1$- to $C_4$-alkyl, such as methyl, ethyl, n-propyl, isopropyl, n-butyl, isobutyl, sec-butyl or tert-butyl, $C_3$- to $C_8$-cycloalkyl, such as cyclopropyl, cyclobutyl, cyclopentyl, cyclohexyl, cycloheptyl or cyclooctyl, preferably cyclopentyl, cyclohexyl or cyclooctyl, aryl, such as phenyl, 1-naphthyl, 2-naphthyl, 1-anthryl, 2-anthryl or 9-anthryl, preferably phenyl, 1-naphthyl or 2-naphthyl, particularly preferably phenyl, $C_7$- to $C_{20}$-aralkyl, preferably $C_7$- to $C_{12}$-phenylalkyl, such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl or 4-phenylbutyl, particularly preferably benzyl, 1-phenethyl or 2-phenethyl, $R^5$ hydrogen, $C_1$- to $C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl or isododecyl, preferably $C_1$- to $C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl or isooctyl, particularly preferably $C_1$- to $C_4$-alkyl, such as methyl, ethyl, n-propyl, isopropyl, n-butyl, isobutyl, sec-butyl or tert-butyl.

The tetrahydropyran-4-carboxylic esters II required for the novel reaction can be obtained from diethyl tetrahydropyran-4,4-dicarboxylate (i. Chem. Soc. (1952), page 2268). The tetrahydropyran-4-carboxylic esters of the formula II can be obtained from the diethyl ester by hydrolysis using potassium hydroxide to give tetrahydropyran-4,4-dicarboxylic acid, subsequent thermal decarboxylation to give tetrahydropyran-4-carboxylic acid, subsequent reaction with thionyl chloride to give tetrahydropyran-4-carbonyl chloride and subsequent esterification with alcohols (J. Chem. Soc. (1930), p. 2525).

The 4-hydroxymethyltetrahydropyrans which can be prepared according to the invention are particularly suitable as precursors for the preparation of cropprotection agents.

EXAMPLES

The catalysts used in the examples had the following compositions (data in % by weight):

| Catalyst | Composition |
| --- | --- |
| A | 64% CoO; 18% CuO; 7% $MnO_2$; 4% $MoO_2$; 0.2% $Na_2O$ |
| B | 50% NiO; 30% $ZrO_2$; 18% CuO, 1.5% $MoO_2$; 0.2% $Na_2O$ |
| C | 35% CuO; 65% $Al_2O_3$ |
| D | 52% CuO; 48% $Al_2O_3$ |
| E | 50% Cu; 48% Cr; 2% $MnO_2$ |
| F | 3% Pd; 3% Re; 94% $TiO_2$ |
| G | 1% Ru; 1.2% Sn; 1.3% B; 96.5% $Al_2O_3$ |

EXAMPLE 1

The hydrogenation was carried out in a 300 ml stirred autoclave containing 10 g of catalyst A and 100 ml of methyl tetrahydropyran-4-carboxylate. The reaction conditions were 250° C./260 bar of hydrogen for 12 hours.

Analysis of the liquid reaction product by gas chromatography gave a yield of 97%.

EXAMPLES 2 TO 7

The hydrogenations were carried out by a method similar to that of Example 1. The catalysts used in each case are shown in Table 1 together with the proportions of methyl tetrahydropyran-4-carboxylate and 4-hydroxymethyltetrahydropyran in the reaction product.

TABLE 1

| Catalyst | Methyl tetrahydropyran-4-carboxylate [GC area %] | 4-Hydroxymethyl-tetrahydropyran [GC area %] |
| --- | --- | --- |
| B | 0.8 | 97 |
| C | 0.2 | 96 |
| D | 1.5 | 90 |
| E | 1.5 | 94 |
| F | 2.5 | 81 |
| G | 0.3 | 94 |

EXAMPLES 8 TO 11

The reactions were carried out by a method similar to those of Example 1 in a 2 l stirred autoclave containing 1 l of methyl tetrahydropyran-4-carboxylate and 50 g of catalyst. The reaction conditions were 250° C./300 bar of hydrogen for 60 hours.

The catalysts used in each case are shown in Table 2 together with the composition of the hydrogenation product.

TABLE 2

| Catalyst | Methyl tetrahydropyran-4-carboxylate [GC area %] | 4-Hydroxymethyl-tetrahydropyran [GC area %] |
| --- | --- | --- |
| A | 2.5 | 92 |
| C | 0.4 | 96 |
| D | — | 72 |
| G | 0.7 | 87 |

EXAMPLE 12

The hydrogenation was carried out in a tubular reactor (length 2000 mm, diameter 16 mm) containing catalyst C in a fixed bed. The reactor was heated to the reaction temperature by means of an external heating jacket containing oil. The gaseous and liquid starting materials were passed through the reactor, top to bottom. The hydrogenation product was decompressed and separated into its gaseous and liquid constituents in a gas/liquid separator.

The catalyst was employed in the form of 2.5 to 4 mm grit and was activated with hydrogen before the hydrogenation was commenced.

At an overall pressure of 300 bar and at 250° C., 0.3 kg of methyl tetrahydropyran-4-carboxylate and 0.5 M³ of hydrogen were fed hourly to the reactor per litre of catalyst.

Analysis of the liquid reaction product by gas chromatography gave a conversion of 100% and a selectivity of 97%.

We claim:

1. A process for the preparation of 4-hydroxymethyl-tetrahydropyrans of the formula I

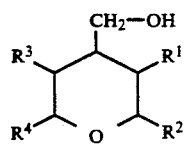

where $R^1$, $R^2$, $R^3$ and $R^4$ are hydrogen, $C_1$- to $C_{12}$-alkyl $C_3$- to $C_8$-cycloalkyl, aryl or $C_7$- to $C_{20}$-aralkyl, which comprises reacting a tetrahydropyrancarboxylic ester of the formula II

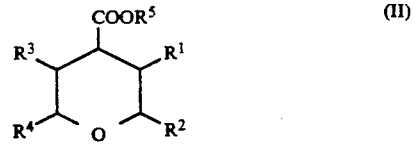

where $R^1$, $R^2$, $R^3$ and $R^4$ are as defined above, and $R^5$ is hydrogen or $C_1$- to $C_{12}$-alkyl, at from 50° to 400° C. and at from 1 to 400 bar in the presence of hydrogen and a hydrogenation catalyst.

2. A process as claimed in claim 1, wherein the hydrogenation catalyst used contains copper and/or one or more metals of elements from sub-group VII and/or VIII of the Periodic Table of the Elements.

3. A process as claimed in claim 1, which is carried out in a liquid phase.

* * * * *